United States Patent [19]

Perrine

[11] Patent Number: 4,822,821

[45] Date of Patent: Apr. 18, 1989

[54] METHOD FOR AUGMENTING FETAL HEMOGLOBIN

[75] Inventor: Susan Perrine, Stanford, Calif.

[73] Assignee: Children's Hospital Medical Center of Northern California, Oakland, Calif.

[21] Appl. No.: 917,805

[22] Filed: Oct. 10, 1986

[51] Int. Cl.$^4$ .................. A61K 31/19; A61K 31/195; A61K 31/26

[52] U.S. Cl. ........................................ 514/557; 514/2; 514/3; 514/4; 514/561; 514/815

[58] Field of Search ................. 514/3, 4, 815, 561, 514/557

[56] References Cited

PUBLICATIONS

Karlsson–*Ann. Rev. Biochem* 1985, 54 1071–1101.
"Development of Therapeutic Agents for Sickle Cell Disease", Rosa et al., North–Holland Pub. Co. Amsterdam–N.Y.–Oxyford, pp. 129–137.

*Primary Examiner*—Frederick E. Waddell
*Attorney, Agent, or Firm*—Flehr, Hohbach, Test, Albritton & Herbert

[57] ABSTRACT

A method is provided for inhibiting the $\gamma$ to $\beta$-globin switching in subjects afflicted with $\beta$-globin disorders. The method is particularly adapted for ameliorating the clinical symptoms of sickle cell anemia by periodically introducing into the bloodstream of the subject prior to natural completion of the switching process $\alpha$-amino-n-butyric acid, butyric acid, isomers or salts thereof, insulin, histone deacetylase inhibitors, or mixtures thereof.

5 Claims, No Drawings

METHOD FOR AUGMENTING FETAL HEMOGLOBIN

The present invention is directed to a method for inhibiting or reversing the switching in in vivo or in vitro from production of $\gamma$ to $\beta$-globin, thus augmenting the production of fetal hemoglobin. In particular, the present invention is directed to a method for controlling the fetal hemoglobin switch by introducing into the bloodstream of the fetus or child or into erythroid cultures a butyric acid derivative or insulin.

BACKGROUND OF THE INVENTION

Normal adult hemoglobin comprises four globin proteins, two of which are $\alpha$ proteins and two of which are $\beta$ proteins. Diseases known as sickle cell syndromes are associated with disorders in the $\beta$ chain of the hemoglobin. However, in mammals, and particularly in humans, during fetal development, the fetus produces a fetal hemoglobin which comprises, instead of $\beta$-globin proteins, two $\gamma$-globin proteins. At some point during fetal development or infancy, depending on the particular species and individual, there is a so-called globin switch wherein the erythrocytes in the fetus switch from making predominantly $\gamma$-globin to making predominantly $\beta$-globin. It has been observed, however, that increased levels of fetal hemoglobin (derived from $\gamma$-globin) ameliorate the severity of sickling disorders. It has also been observed that subjects heterozygous for hereditary persistence of fetal hemoglobin syndromes (HPFH) and sickling hemoglobin (HbS) are clinically asymptomatic of sickle cell anemia. Also, infants with sickle cell anemia do not usually develop the symptoms of the disease until approximately four months of age when their fetal hemoglobin levels decrease. These observations suggest that a method for increasing the levels of fetal hemoglobin would be beneficial to patients with sickle cell syndromes.

It is thus an object o the present invention to provide a method for inhibiting or reversing the $\gamma$ to $\beta$-globin switch in a fetus or infant to maintain increased fetal hemoglobin levels in those individuals with sickle cell syndromes.

Since inhibition of the $\gamma$ to $\beta$-globin gene switch has been observed in infants of diabetic mothers (IDM), it appears that disturbances in normal metabolites in the bloodstream might disrupt a normally timed and fixed gene-switch. Two metabolites, insulin and butyric acid, have been observed as being elevated in infants of diabetic mothers. Some investigators have shown that factors in serum can effect the $\gamma$ to $\beta$-globin switching, particularly around the time the switch occurs. There has been, however, heretofore no development of a non-toxic therapeutic method or natural agent to increase fetal hemoglobin in subjects with sickle cell disease.

It is thus another object of the present invention to provide an agent for maintaining a high level of $\gamma$ chain synthesis (thereby maintaining high fetal hemoglobin levels), without toxicity and long term side effects, by using a physiologic factor rather than a chemotherapeutic agent.

SUMMARY OF THE INVENTION

The present invention provides a method for ameliorating $\beta$-globin disorders in mammals comprising the step of periodically introducing into the bloodstream of said mammal during its gestation period and/or early infancy and thereafter, an amount of a compound selected from the group consisting of $\alpha$-amino-n-butyric acid, butyric acid, isomers and non-toxic salts thereof, insulin, histone deacetylase inhibitors, and mixtures of these sufficient to inhibit or reverse fetal $\gamma$ to $\beta$-globin switching. The method according to the present invention is particularly useful for ameliorating in humans the clinical effects of sickle cell anemia.

DESCRIPTION OF THE INVENTION

The present invention provides a method for ameliorating the clinical effects of $\beta$-globin disorders, prticularly the disorder of sickle cell anemia and thalassemias. The present invention is advantageous in that the compounds utilized are physiologic factors, i.e., natural metabolites found in the bloodstream of mammals and are thus, when introduced into the bloodstream, not likely to have toxic or undesirable long term side effects.

In accordance with the present invention, $\alpha$-amino-n-butyric acid, n-butyric acid, isomers or non-toxic salts thereof, insulin, histone deacetylase inhibitors, or mixtures of these are introduced into the bloodstream of the subject shown to or suspected of having a $\beta$-globin disorder, such as sickle cell anemia or thalassemias. The foregoing may be administered as their non-toxic salts, such as their sodium salts, potassium salts, and the like. Furthermore, isomers (including optical isomers) and homologs of butyric acid and amino-butyric acid having switch-inhibiting or reversing activity may be utilized. Preferred compounds are L-$\alpha$-amino-n-butyric acid, DL-$\alpha$-amino-n-butyric acid and sodium butyrate.

Among the compounds used in accordance with the present invention, sodium butyrate is a known inhibitor of histone deacetylase. While not intending to be limited by a theory of biological mechanism on which the invention operates, it is believed that inhibition of histone deacetylase is an important aspect to the ultimate inhibition or reversal of the globin switch. Thus, the use of other compounds having histone acetylase inhibiting activity is contemplated to be within the scope of the invention.

The method used to introduce the compound will be any convenient method normally used to introduce pharmaceuticals into the bloodstream, such as by injection, infusion, and the like. Oral or parenteral administration may also be utilized.

The exact size of an effective dose of a compound according to the method of the present invention will depend on a number of factors including the particular recipient and the severity of condition, thus the route of administration will be ultimately at the discretion of the attendant physician.

While it is possible to utilize the compounds in vivo as a raw chemical, it is preferable to present them as a pharmaceutical formulation preparation. The formulation of the present invention comprises a compound as previously described together with one or more acceptable carriers therefor and, optionally other therapeutic ingredients. The carriers must be acceptable in the sense of being compatible with other ingredients of the formulation and not dilitary as to the recipient.

For oral administration, the formulations may be presented as discrete units such as capsules, or tablets each containing a predetermined amount of the active ingredient, as a powder or granules, as a solution or suspension in an aqueous or nonaqueous liquid, as an oil in water liquid emulsion or as a water in oil liquid emulsion.

Formulations for parenternal administration include aqueous or nonaqueous sterile injection solutions which may contain antioxidants, buffers, bacteriostats and solutes which render the formulation isotonic with the blood of the intended recipient. The formulation may be presented in dose unit or multi-dose containers such as ampules or vials and may be stored in a freeze-dried condition requiring only the addition of a sterile liquid carrier, for example water, for injections.

Preferred unit dosage formulations are those containing a daily dose or a unit daily subdose, or an appropriate fraction thereof.

As further application of the compounds according to the present method, they may be utilized in vitro to cell cultures taken from patients to determine the potential efficacy of further treatment for the β-globin disorders, such as sickle cell anemia. The compounds may be thus used in vitro in cell cultures from patients to determine whether further addition of one of the compounds would result in continued inhibition or reversal of the globin switch.

The frequency and dosages of administration of the above compounds will depend upon when the compound is introduced, whether the subject is a fetus or an infant, the size and weight of the subject, the condition of the pregnant mother, and the like. Generally, injections beginning at a dosage of about 12 mg/kg body weight per day during gestation, particularly prior to the thirty-second week of gestation in humans, will delay the γ to β switching. Higher dosages, up to about 500 mg/kg may be utilized at the discretion of the physician. Since apparently the switching process is not complete in humans until approximately four months after birth, treatment may be initiated after birth up until about the fourth month of infancy and continued as long as necessary to maintain enhanced fetal hemoglobin levels in the patient.

All treatment should preferably occur prior to the fourth month of infancy since the γ to β switching process is difficult to reverse. Although treatment with one of the above compounds prior to the fourth month of infancy will inhibit the γ to β-switching process, treatment subsequent to that period may also achieve the desired clinical results, i.e., the amelioration of the effects of the β-globin disorder. Therefore, if the switching process is inhibited even to the extent of 10 to 20% (that is, the subject makes 10 to 20% more γ-globin than would be expected if the switch were allowed to occur), this may be sufficient to ameliorate the symptoms of the disease.

The method according to the present invention may be utilized in vivo, or in vitro as a diagnostic test. For the in vitro test erythroid cultures, such as that obtained from cord blood mononuclear cells in Iscove's Modified Dulbcco's Medium with 0.9% methylcellulose, may be used as described by Stamatoyannopoulous et al., Blood, 54, 440–450 (1979) and Friedman et al., J. Clin. Invest., 75, 1359–1368 (1985). The cultures may be formed with and without the addition of various metabolites whose concentrations are observed to increase in infants of diabetic mothers (IDM). To show the effect of such factors, insulin (0.1–100 ng/ml), Insulin Growth Factor I (4–10 ng/ml), Isoleucine (4–10 mcg/ml), and butyric acid (0.01–10 mM) were added to the cultures. Some cultures were performed in 95% nitrogen to simulate a hypoxic intrauterine environment, and IDM plasma was used instead of fetal calf serum in some cultures. Colonies were harvested and incubated with $^3$H-leucine under the same culture conditions for the last 24 hours. Globin production was analyzed by electrophoresis on Triton-urea gels, autoradiography, and densitometry and by radioligand immunoassay of the total and fetal hemoglobin in pg per Bfu-e-derived cell was performed as described in Stamatoyannopoulous et al. and Friedman et al., ibid. In 10 Cfu-e (colony-forming unit-erythroid) cultures from five normal infants and five term IDM mean β-globin synthesis (expressed as percent of total non-α synthesis), was 42.3% β-globin and 17.3% respectively. This is equivalent to the β-globin levels produced in infants' reticulocytes. This difference in percent β-globin synthesis between the IDM and normal infant Cfu-e was ($p < 0.001$, Student's t-test) and indicates that these relatively late erythroid progenitors are committed to a pattern of globin production in the fetal environment. The percentage of β-globin synthesized by Bfu-e (burst-forming unit-erythroid) from normal term infants did not differ statistically from the percentage produced by their Cfu-e. However, Bfu-e from IDM produced a significantly higher percentage of the β-globin then did the infants Cfu-e and reticulocytes ($p < 0.05$). This difference indicates that switching to increased β-globin production occurred once the more primitive progenitors were removed from the abnormal intrauterine environment or that the process began in vivo. Thus, the apparent in vitro switching by Bfu-e cultures from premature infants of less than 33 weeks gestation and from term IDM (pre-switch infants) is an assay system for testing the effect on globin switching of physiological parameters peculiar to the diabetic intrauterine environment, in which the globin switch is delayed. The addition of insulin, IGF-I, isoleucine, or low oxygen conditions cause the Bfu-e to synthesize the equivalent more β-globin than control cultures.

Sodium butyrate (at 0.1 mM concentrations), caused Bfu-e from pre-switch infants to synthesize significantly less β-globin than did Bfu-e in control cultures. This affect of sodium butyrate was not found consistently in infants in whom the switch had occurred before birth, however, increased γ-globin synthesis was found consistently with α-amino-n-butyric acid. A significant increase in accumulation of hemoglobin F in the cord blood erythroid colonies also occurred in nine out of eleven cultures from seven infants, grown in the presence of sodium-butyrate compared to control cultures ($p < 0.05$). This effect on increasing hemoglobin F in culture was not due to toxicity since the pH of the culture media was not effected, and similar numbers of Bfu-e and Cfu-e were found in cultures grown in the presence or absence of the butyrates. Radioimmunoassay of Bfu-e hemoglobin indicates complete hemoglobinization ($>15$ pg/cell) in the presence of butyrate, demonstrating that the observed increase in hemoglobin F synthesis and accumulation were not an artifact of retardation of globin production.

The following examples are provided by way of illustration, however, the invention is not intended to be limited in any manner thereby.

EXAMPLE 1

C57 mice have a murine embryonic-to-adult globin gene switch that occurs by day 13 of gestation; (mice have a minor β globin that is not expressed at a high rate, as are the human fetal γ chains). Whether insulin and/or butyrate is prolonging γ globin expression or, rather, inhibiting β globin expression is established by studying the normal developing mouse, where embryonic ζ-globin is produced until day 11-12 of gestation, and β minor and major produced from day 13 on. Effects of these metabolites on the normal murine embryonic to β-globin switch determine that α-amino-n-butyric acid or maternal diabetes will delay the murine developmental embryonic to adult globin switch.

To evaluate the effects of insulin, mice are made diabetic by 5 daily injections (IP) of streptozotocin (50 mg/kg) delivered in citrate buffer, pH 4.2. This treatment induces hyperglycemia in the female (mother) mice, producing reactive hyperglycemia in the developing fetuses. Glucose levels are monitored from tail vein blood by glucoscan and insulin treatment is given as required. For monitoring $G_\gamma$ or embryonic globin expression, the yolk sac cells are dissected out on days 11-12. Nucleated erythrocytes from the yolk sac can be obtained by bleeding from the umbilical cord up to day 12, when >95% of the cells are primitive nucleated RBCs. After day 12, when the fetal liver becomes the major site of erythropoiesis, fetal erythrocytes are obtained from the liver by dissection. For monitoring murine embryonic and β-globin expression, erythroblasts are assayed after day 12. Globin gene expression in transgenic mice, who may not make detectable globin protein, are monitored by mRNA hybridization to a labelled γ or β RNA probe (Riboprobe Kit), and electrophoresis on an acrylamide/urea gel. For assaying normal developmental murine globin expression and potential inhibition, the embryonic and adult globin chains are separated on Rovera-Triton gels and autoradiography as described above.

To evaluate the effects of butyric acid on gene expression (with and without insulin), γ-amino-n-butyric acid in PBS is injected intraperitoneally into the adult females and plasma levels from tail veins are monitored on an amino acid analyzer until appropriate levels are obtained. This metabolite is actively transported across the placenta and a concentration 1.6× the maternal plasma level are achieved in embryos. Levels needed in the fetus are 0.1 to 5 mM.

If γ-globin or murine embyronic globin expression is found to continue past the usual 11-12 days under any of these conditions, treatment may continue indefinitely thereafter. This will produce continued embryonic murine globin expression throughout the gestation, and ultimately for the lifespan of the mouse.

EXAMPLE 2

Cultures of erythroid progenitors from blood obtained during the first three years of life of Hb SS (sickle cell syndrome) infants are tested. It was found that butyric acid increases γ-globin synthesis in infant cord blood erythroid colonies, including 5 of 7 SS samples from infants, even when the infants' reticulocytes and control colonies (Bfu-e) synthesize nearly all β-globin.

EXAMPLE 3

In peripheral blood erythroid cultures established from infant sickle cell anemia patients from 5/7 patients under age 3 years, it was found that butyrate enhances γ globin synthesis by approximately 14% compared to control cultures from the same patients. This would achieve corresponding Hb F synthetic levels of greater than 20% in most patients.

EXAMPLE 4

A Dexter culture is established from cord blood from an infant with sickle cell anemia whose mother has diabetes. This infant was prenatally diagnosed and has almost no $\beta^s$ globin on electrophoresis. Progenitors assayed weekly for globin synthesis from this infant's erythroid progenitors cultured in the presence and absence of α amino-n-butyric acid and insulin showed that the combination of these two agents prevented switching at two weeks. Her control cells switched from 9% $\beta^s$ globin to 20%. The treated cells still synthesize only 9% $\beta^s$ globin.

What is claimed is:

1. A method for ameliorating sickle cell anemia in a mammal comprising the step of introducing into the bloodstream of said mammal periodically during its gestation period and/or infancy, a compound selected from the group consisting α-amino-n-butyric acid, butyric acid, isomers and non-toxic salts thereof, insulin, and mixtures thereof, in an amount and frequency and duration of life sufficient to inhibit or reverse fetal τ to β-globin switching.

2. A method of ameliorating thalassemia in a mammal comprising the step of introducing into the bloodstream of said mammal periodically during its gestation period and/or infancy, a compound selected from the group consisting α-amino-n-butyric acid, butyric acid, isomers and non-toxic salts thereof, insulin, and mixtures thereof, in an amount and frequency and duration of life sufficient to inhibit or reverse fetal τ to β-globin switching.

3. A method according to claim 1 or 2 wherein said compound is α-amino-n-butyric acid.

4. A method according to claim 1 or 2 wherein said compound is sodium butyrate.

5. A method according to claim 1 or 2 wherein γ to β-globin switching is inhibited to the extent that γ-globin synthesis in said mammal remains at 10 to 20% above normal levels after birth.

* * * * *